US009689883B2

(12) United States Patent
Oonuma et al.

(10) Patent No.: US 9,689,883 B2
(45) Date of Patent: Jun. 27, 2017

(54) AUTOMATED ANALYZER (71) Applicant: HITACHI HIGH-TECHNOLOGIES CORPORATION, Tokyo (JP)

(72) Inventors: Mitsuru Oonuma, Tokyo (JP); Yoko Sato, Tokyo (JP); Takashi Yamamoto, Tokyo (JP); Takeshi Setomaru, Tokyo (JP); Hideyasu Chiba, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/911,912

(22) PCT Filed: Jul. 31, 2014

(86) PCT No.: PCT/JP2014/070167
§ 371 (c)(1),
(2) Date: Feb. 12, 2016

(87) PCT Pub. No.: WO2015/029685
PCT Pub. Date: Mar. 5, 2015

(65) Prior Publication Data
US 2016/0195562 A1 Jul. 7, 2016

(30) Foreign Application Priority Data

Sep. 2, 2013 (JP) ................. 2013-181333

(51) Int. Cl.
G01N 35/02 (2006.01)
G01N 35/10 (2006.01)
(Continued)

(52) U.S. Cl.
CPC ..... G01N 35/025 (2013.01); G01N 35/00871 (2013.01); G01N 35/04 (2013.01);
(Continued)

(58) Field of Classification Search
None
See application file for complete search history.

(56) References Cited

U.S. PATENT DOCUMENTS 4,338,279 A 7/1982 Orimo et al.
5,855,847 A * 1/1999 Oonuma ................ G01N 35/02
422/63

(Continued)

FOREIGN PATENT DOCUMENTS

CN 202676602 U 1/2013
JP 55-136957 A 10/1980
(Continued)

OTHER PUBLICATIONS

Japanese Office Action in corresponding Japanese Application No. 2013-181333, dated Jan. 24, 2017.*
(Continued)

Primary Examiner — P. Kathryn Wright
(74) Attorney, Agent, or Firm — Mattingly & Malur, PC (57) ABSTRACT To provide an automated analyzer with a built-in, user-friendly printer that can avoid contamination of printed paper of the printer by having a housing front wall 102 provided in a recessed manner from a front end 101 of a housing upper portion that has disposed thereon a sample disc 110, a reagent disc 120, a reaction disc, a sample dispensing mechanism, and a reagent dispensing mechanism, and by having a printer 200 and a paper receptacle 210 disposed on the housing front wall. The front end portion of the housing upper portion that projects beyond the housing front wall serves as eaves, thereby preventing a sample or a reagent that may be spilled on the housing upper portion from staining the printer or printing paper.

2 Claims, 7 Drawing Sheets (51) Int. Cl.
  *G01N 35/00* (2006.01)
  *G01N 35/04* (2006.01)
(52) U.S. Cl.
  CPC .............. *G01N 35/1065* (2013.01); *G01N 2035/00306* (2013.01); *G01N 2035/0441* (2013.01); *G01N 2035/0443* (2013.01); *G01N 2035/0444* (2013.01); *G01N 2035/0496* (2013.01)

(56) References Cited

U.S. PATENT DOCUMENTS

| | | | |
|---|---|---|---|
| 6,440,369 | B1 | 8/2002 | Oonuma et al. |
| 2007/0280854 | A1 | 12/2007 | Matsumoto et al. |
| 2009/0232574 | A1* | 9/2009 | Takahashi .............. B41J 15/042 400/613 |
| 2011/0184536 | A1* | 7/2011 | Tanoshima ....... G01N 35/00871 700/73 |
| 2014/0241945 | A1 | 8/2014 | Oonuma et al. |

FOREIGN PATENT DOCUMENTS

| | | |
|---|---|---|
| JP | 03-078646 A | 4/1991 |
| JP | 04-244962 A | 9/1992 |
| JP | 8-94623 A | 4/1996 |
| JP | 9-127120 A | 5/1997 |
| JP | 2003-305917 A | 10/2003 |
| JP | 2007-322208 A | 12/2007 |
| JP | 2011-153960 A | 8/2011 |
| JP | 2013-072799 A | 4/2013 |
| WO | 2013/046913 A1 | 4/2013 |

OTHER PUBLICATIONS

International Search Report of PCT/JP2014/070167.
Chinese Office Action in corresponding Chinese Application No. 201480045441.1 dated Aug. 10, 2016.
Extended European Search Report received in corresponding European Application No. 1483946.8 dated Mar. 7, 2017.

* cited by examiner

AUTOMATED ANALYZER

TECHNICAL FIELD

The present invention relates to an automated analyzer for analyzing a biological sample, such as blood or urine.

BACKGROUND ART

A clinical examination for medical diagnosis may involve a biochemical analysis or an immunological analysis of protein, sugars, lipids, enzymes, hormones, inorganic ions, disease markers, and the like in a biological sample, such as blood or urine. During the clinical examination, a plurality of examination items should be processed reliably and at high speed. Thus, a large part of the examination is executed by an automated analyzer.

The reactions measured by the automated analyzer mainly include two types, one a color reaction of a substrate and an enzyme, and the other an immunoreaction of an antigen and an antibody. The analysis using the former reaction is referred to as a biochemical analysis, where examination items include LDH, ALP, AST and the like. A biochemical analysis is performed by, for example, measuring the absorbance of a reaction solution to be analyzed that has been obtained by mixing a sample, such as serum, with a desired reagent and causing a reaction therebetween. An analysis using the latter reaction is referred to as an immunoassay, where examination items include CRP, IgG, RF, and the like. The substances to be measured by the latter include examination items for which quantification in a low concentration region having low blood concentration is required. For such items, a latex immunoassay is used where latex particles with surfaces sensitized (bonded) with antibodies are used as a sensitizer.

Some automated analyzers have printers attached thereto for printing analysis results and the like on recording paper and outputting the results. Patent Literature 1 discloses a biochemical analyzer that has a printer disposed in an upper portion of its housing. In addition, Patent Literature 2 discloses a biochemical analyzer that has a printer disposed on the front portion of the analyzer.

CITATION LIST

Patent Literature

Patent Literature 1: JP H03-78646 A
Patent Literature 2: JP 2007-322208 A

SUMMARY OF INVENTION

Technical Problem

When a printer is built into a small-size automated analyzer, it is often the case that a printer that is small-size, lightweight and easy to maintain, like a thermal-transfer printer, is used. In such a case, a continuous roll of paper, which is obtained by winding paper in a roll, is used as recording paper. A variety of places of an automated analyzer is considered as a place on which a printer is to be disposed, such as an upper face of the analyzer, a side face of the analyzer, and a front face of the analyzer. A roll of paper is, after being printed, ejected from the printer as a long, continuous sheet of paper. When a printer is disposed on the upper face of the analyzer, recording paper may be ejected in the forward direction or the backward direction of the analyzer. When a printer is disposed on the side face of the analyzer, recording paper is ejected in the lateral direction of the analyzer. Further, when a printer is disposed on the front face of the analyzer, recording paper is ejected in the forward direction of the analyzer.

Herein, suppose that printed paper is ejected in the backward direction of the analyzer. Then, the recorded paper is ejected such that it hangs down behind the analyzer. Thus, space is needed between the analyzer and the wall, and it is thus impossible to dispose the analyzer in proximity to the wall. In addition, there is another problem in that taking out a recorded roll of paper from behind the automated analyzer, for example, is burdensome. Meanwhile, when printed paper is ejected in the lateral direction of the analyzer, it is impossible to dispose another device in proximity to the side face of the analyzer on the paper ejection side, which is problematic in terms of the efficient use of space. Further, in the case of an automated analyzer that handles a liquid, such as a biological sample or a liquid reagent, there is a possibility that the upper face of the analyzer on which a biological sample or a reagent is put may become contaminated with the liquid that may be spilled even if great care is taken. When a continuous roll of paper is transferred on the upper face of the automated analyzer, there is a possibility that a liquid that is spilled on the upper face of the analyzer may stick to and contaminate the paper. Therefore, it is desirable to avoid using a configuration in which recording paper is transferred on the upper face of the analyzer.

As described above, from a perspective of improving the operator's workability and saving the space for disposing the automated analyzer, it is desirable to dispose a printer, which is to be built into the analyzer, on the front wall of the analyzer. However, in the case of an automated analyzer that handles a liquid, there may be cases where a sample or a reagent that is spilled by mistake may fall from the upper face of the analyzer along the front wall of the analyzer. In such cases, circumstances may arise in which a printer that is disposed on the front wall of the analyzer or a printed continuous roll of paper that is ejected from the printer become contaminated with the sample or the reagent. When recording paper is contaminated with a sample or a reagent, not only does the printed text become unclear, but also a hygienic problem arises. So far, no particular measure has been taken to avoid such contamination of a roll of paper ejected from the printer.

The present invention provides an automated analyzer with a built-in, user-friendly printer that can avoid contamination of the printer and printed paper with a liquid, such as a sample or a reagent, that may be spilled by mistake.

Solution to Problem

The automated analyzer of the present invention includes a housing upper portion, the housing upper portion having disposed thereon a sample disc holding a plurality of samples, a reagent disc holding a plurality of types of reagents, a reaction disc holding a plurality of reaction cells, a sample dispensing mechanism for dispensing one of the samples into one of the reaction cells held on the reaction disc, and a reagent dispensing mechanism for dispending one of the reagents into the reaction cell held on the reaction disc; a housing front wall provided in a recessed manner from a front end of the housing upper portion; and a printer disposed on the housing front wall. The housing front wall may have a paper receptacle disposed below the printer, the paper receptacle being adapted to receive paper ejected from the printer.

According to such a configuration, the front end portion of the housing upper portion that projects beyond the housing front wall serves as eaves for protecting the printer by covering an area above the printer. Thus, even when a sample or a reagent is spilled on the housing upper portion and drops from the housing upper portion, there is no possibility that the printer or printed paper may become contaminated.

The analyzer may further include a front door provided in an openable/closable manner, the front door covering the housing front wall that has the printer and the paper receptacle disposed thereon. The front door may have an opening that allows paper ejected from the printer to pass therethrough in a state in which the front door is closed.

As a specific configuration, the front door has a window formed in a recessed manner from a door front face at a position corresponding to the printer. The window may be defined by a bottom face, an upper face, right and left side faces, and a lower face, the bottom face being opposite the printer, and the upper face connecting the door front face with the bottom face. The opening may be provided across the bottom face and the lower face.

Herein, the lower face may be formed in a manner tilted downward from the bottom face toward the door front face, and may have a frame shape in which the opening is surrounded from sides of the right and left side faces and the door front face.

The printer may include means for switching an ejection direction in which paper is ejected from the printer.

The printer preferably includes a paper ejection unit that is located closer to a housing than is the front end of the housing upper portion.

Advantageous Effects of Invention

According to the present invention, it is possible to dispose a printer on a front wall of an analyzer while avoiding contamination of printed paper, which is ejected from the printer, with a sample or a reagent.

Other problems, configurations, and advantageous effects will become apparent from the following description of embodiments.

DESCRIPTION OF EMBODIMENTS

Hereinafter, embodiments of the present invention will be described with reference to the accompanying drawings.

Figure 1:
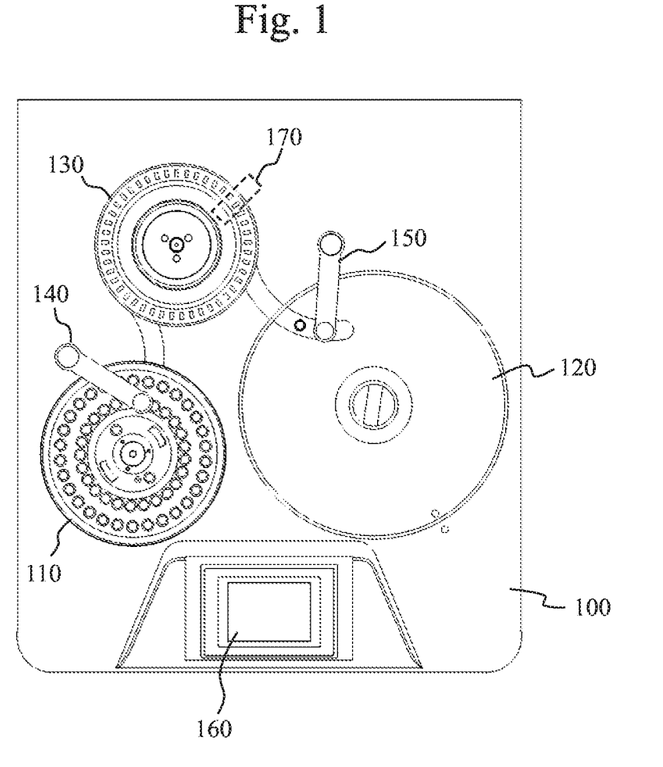
FIG. 1 is a schematic view of the arrangement of elements on a housing upper portion of an automated analyzer.

FIG. 1 is a schematic view of the arrangement of elements on a housing upper portion 100 of an exemplary automated analyzer in accordance with the present invention. The automated analyzer in accordance with this embodiment has disposed on the housing upper portion 100 a sample disc 110, a reagent disc 120, a reaction disc 130, a sample dispensing mechanism 140, and a reagent dispensing mechanism 150. According to this embodiment, on the housing upper portion 100, the reaction disc 130 is disposed in the rear-left, with the reagent disc 120 and the reagent dispensing mechanism 150 disposed to the front-right of the reaction disc 130. In addition, the sample disc 110 and the sample dispensing mechanism 140 are disposed to the front-left of the reaction disc 130. The reagent disc 120 has a refrigeration function for preserving reagents and has a reagent disc lid covering the top of the disc. While the example herein uses a single reagent disc, it goes without saying that a plurality of reagent discs may be disposed, and the number of the reagent dispensing mechanisms may be increased in accordance with the number or the location of the reagent discs. A display unit 160, such as a liquid crystal display, is disposed on the front side of the housing upper portion.

The automated analyzer includes an agitation unit for agitating a mixture solution in a reaction cell, a reaction cell washing unit for washing the reaction cell, a nozzle washing unit for washing nozzles of the dispensing mechanisms, and the like. Inside the housing are provided a variety of devices (not shown) constituting the automated analyzer as well as a power supply for driving such devices, a control mechanism, a constant-temperature bath, a wash pump, and the like. Such components are not important for the configuration of the present invention, and are provided in the conventional automated analyzers. Thus, illustration and detailed description of such components are omitted herein.

The automated analyzer in accordance with this embodiment includes a diffraction grating as a wavelength dispersing element, and measures the absorbance of a sample at a predetermined wavelength. In the housing, a transmitted light beam measurement unit 170 for spectroscopic analysis of a transmitted light beam, which has passed through a reaction solution, is disposed at a prescribed region on the circumference of the reaction disc 130.

Figure 2:
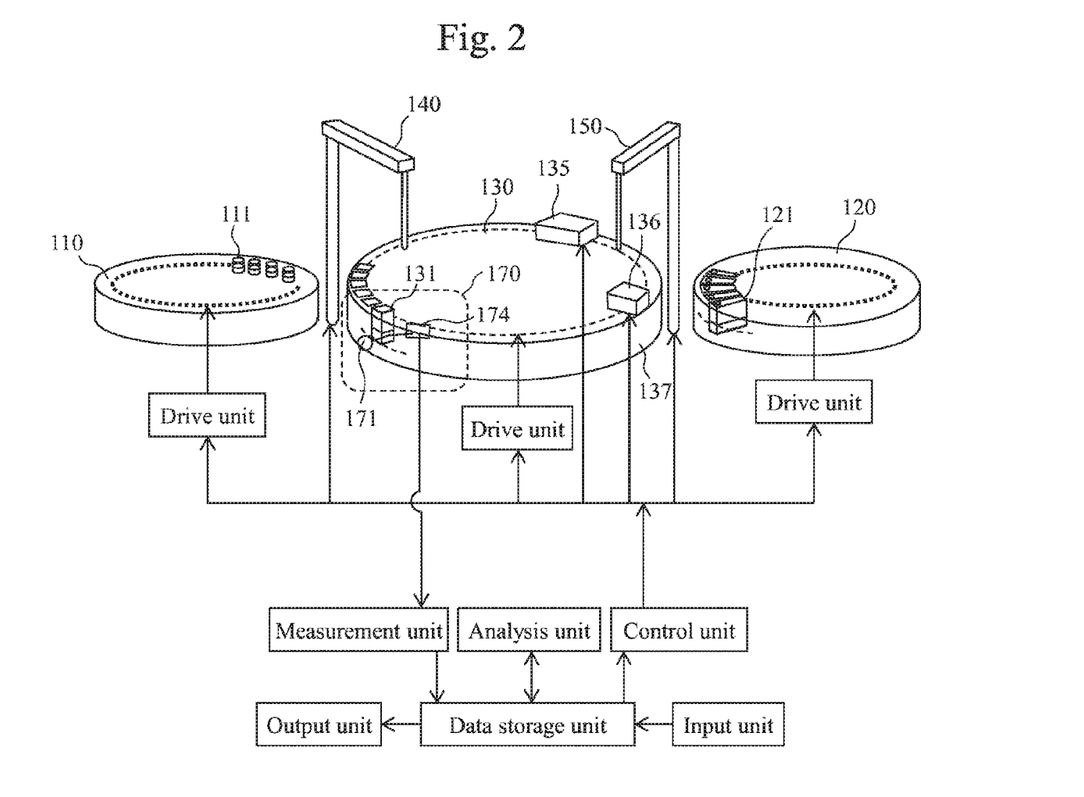
FIG. 2 is a view illustrating an overall configuration example of the automated analyzer.

FIG. 2 is a schematic view illustrating an overall configuration example including a control system of the automated analyzer illustrated in FIG. 1.

A plurality of sample cups 111 containing samples is disposed on the sample disc 110. A plurality of reagent bottles 121 containing reagents is disposed on the reagent disc 120. On the circumference of the reaction disc 130, a plurality of reaction cells 131 for internally mixing the samples and the reagents to obtain reaction solutions is disposed. The sample dispensing mechanism 140 includes an arm, which rotates about a support column, and a nozzle secured to the arm, and dispenses a given amount of a sample from the sample cup 111 to the reaction cell 131. The reagent dispensing mechanism 150 includes an arm, which rotates about a support column, and a nozzle secured to the arm, and dispenses a given amount of a reagent from the reagent bottle 121 to the reaction cell 131. The agitation unit 135 agitates and mixes the sample and the reagent in the reaction cell 131. The reaction cell washing unit 136 causes a reaction solution to be discharged from the reaction cell 131 after an analysis and washes the reaction cell. Then, the next sample is re-dispensed into the washed reaction cell 131 from the sample dispensing mechanism 140, and a new reagent is dispensed thereinto from the reagent dispensing mechanism 150 so that the reaction cell 131 is used for another reaction. The reaction cells 131 are immersed in a constant-temperature fluid 137 in the constant-temperature bath whose temperature and flow rate are controlled, so that the reaction cells 131 and reaction solutions therein are moved while being maintained at a constant temperature. Water is used for the constant-temperature fluid 137, for example, and the temperature of the constant-temperature fluid is adjusted by a control unit to be 37±0.1° C. The transmitted light beam measurement unit 170 is disposed on a part of the circumference of the reaction disc 130.

Figure 3:
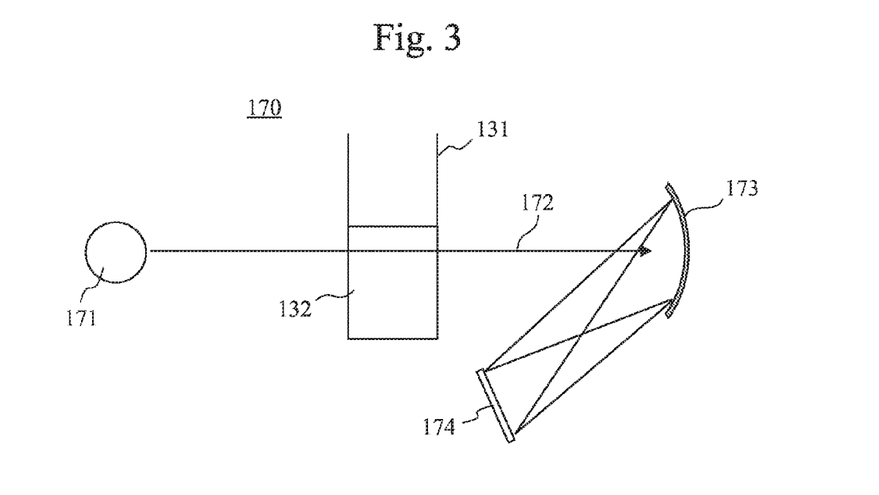
FIG. 3 is a schematic view of a transmitted light beam measurement unit.

FIG. 3 is a schematic view of the transmitted light beam measurement unit. The transmitted light beam measurement unit 170 is disposed in the housing and irradiates the reaction cell 131 with light from a halogen lamp light source 171, and splits, with the diffraction grating 173, a light beam 172 that has passed through a reaction solution 132, which is a mixture of a sample and a reagent, and then receives the split light beams with a photodiode array 174 having photodiodes arranged in an array. The wavelengths of the received light beams are, for example, 340 nm, 405 nm, 450 nm, 480 nm, 505 nm, 546 nm, 570 nm, 600 nm, 660 nm, 700 nm, 750 nm, and 800 nm. Data on the wavelengths of the light beams received by the photodiode array 174 are sent to a data storage unit in a PC via the measurement unit.

The analysis of the amount of a given component in a sample is performed in accordance with following procedures. First, a given amount of a sample in the sample cup III is dispensed into the reaction cell 131 by the sample dispensing mechanism 140. Then, a given amount of a reagent in the reagent bottle 121 is dispensed into the reaction cell 131 by the reagent dispensing mechanism 150. During the dispensing, the sample disc 110, the reagent disc 120, and the reaction disc 130 are rotationally driven by their respective drive units under the control of the control unit, so that the sample cup 111, the reagent bottle 121, and the reaction cell 131 are moved in accordance with the timing of the dispensing mechanisms. Thereafter, the sample and the reagent in the reaction cell 131 are agitated by the agitation unit 135 to obtain a reaction solution 132. A light beam that has passed through the reaction solution 132 is measured each time it passes through the transmitted light beam measurement unit 170 while the reaction disc 130 is rotated, and is sequentially accumulated as reaction process data in the data storage unit from the measurement unit. After the measurement for a given period of time, for example, about 10 minutes, the inside of the reaction cell 131 is washed by the reaction cell washing unit 136, and then, the analysis of the next examination item is performed. In the meantime, if necessary, another reagent is additionally dispensed into the reaction cell 131 by the reagent dispensing mechanism 150, and is agitated by the agitation unit, so that measurement is performed for another given period of time. Accordingly, pieces of reaction process data of a reaction solution having given time intervals are stored in the data storage unit. From the accumulated reaction process data, the amount of the component is analyzed by an analysis unit on the basis of calibration curve data for each examination item. Data necessary for the control of each unit and analysis are input to the data storage unit from an input unit. The calibration curve data is stored in the data storage unit. A variety of pieces of data, results, and alarms are output by an output unit via display, for example.

Figure 4:
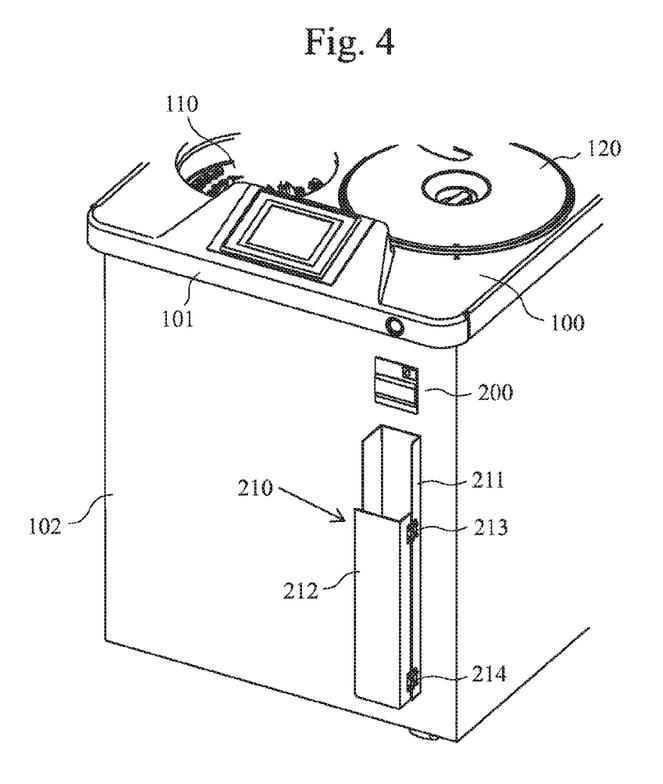
FIG. 4 is a schematic view of an embodiment of the automated analyzer in accordance with the present invention.

FIG. 4 is a schematic view of an embodiment of the automated analyzer in accordance with the present invention. FIG. 4 illustrates only the primary portions, and illustrates the view of the housing upper portion and the front wall.

A front end 101 of the housing upper portion 100, which has the sample disc 110 and the reagent disc 120 disposed thereon, projects beyond a housing front wall 102. In other words, the housing front wall 102 is recessed from the front end 101 of the housing upper portion 100. The housing front wall 102 has a printer 200 disposed thereon as well as a paper receptacle 210 disposed below the printer 200 for receiving a printed roll of paper ejected from the printer. In this embodiment, the printer 200 is constructed such that its main body is stored in the housing through insertion via an opening provided in the housing front wall 102, and only a paper ejection unit of the printer is exposed to the outside. The paper receptacle 210 includes a paper guiding unit 211 secured to the housing front wall 102, and a cover 212 attached to the paper guiding unit 211 with hinges 213 and 214. While the printer is used, side faces of the paper guiding unit 211 are covered with the cover 212 as shown so that a printed continuous roll of paper that is output from the printer 200 is received by and accumulated in a space, which has an open top and a closed bottom, formed in the receptacle. After printing is complete, the roll of paper is cut with a cutter provided to the printer 200, and the cover 212 of the paper receptacle 210 is opened to remove the printed paper stored in the receptacle.

Figure 5:
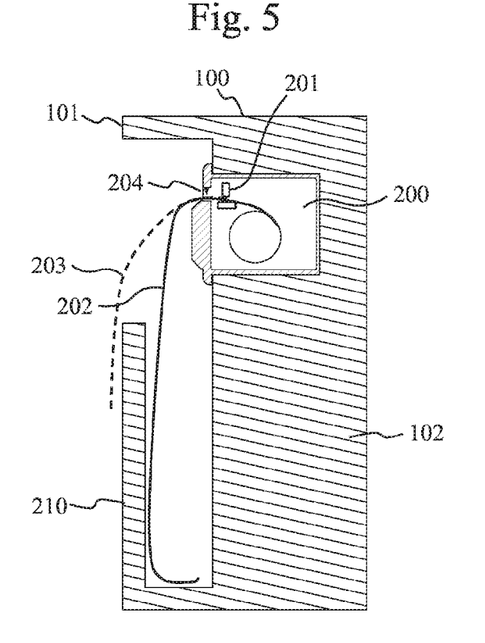
FIG. 5 is a schematic cross-sectional view of an example of a housing front wall, which includes a printer and a paper receptacle, and a housing upper portion connected thereto.

FIG. 5 is a schematic cross-sectional view of the housing front wall, which includes the printer and the paper receptacle, and a housing upper portion connected thereto. The housing upper portion 100 is formed such that its front end 101 projects forward beyond the housing front wall 102. In other words, the housing front wall 102 is recessed from the front end 101 of the housing upper portion 100, and the housing upper portion 100 covers a portion above the printer 200 in an eaves-like shape. Thus, the printer 200 is disposed such that the paper ejection unit thereof is located on the side closer to the housing than is the front end 101 of the housing upper portion 100 that constitutes the eaves. A roll of paper printed by a printing unit 201 of the printer 200 can be guided to and stored into the paper receptacle 210 as indicated by the solid line 202, or be guided to the outside of the paper receptacle 210 as indicated by the dashed line 203, with an end of the paper guided with fingers or the like when ejection starts, for example. The printer 200 includes a cutter 204 for cutting paper.

With the arrangement in this embodiment, the following advantageous effects are obtained. The housing upper portion 100 of the automated analyzer has disposed thereon the sample disc 110 holding a number of sample cups 111 and the reagent disc 120 holding a number of reagent bottles 121, as described with reference to FIGS. 1 and 2. When starting an analysis, it is first necessary to set the sample cups 111 containing samples on the sample disc 110, and such operation is performed manually by the operator. An operation of setting the sample cuts 111 on the sample disc 110 is also necessary in performing an interrupt analysis during the execution of a series of analyses. In such an operation of setting the sample cups 111 on the sample disc 110, it is impossible to say conclusively that samples are never spilled by mistake.

Further, as a reagent to be used may differ from analysis item to analysis item, there may be cases where, among a plurality of types of reagents held on the reagent disc, some reagent gradually runs short and thus should be replenished during the consecutive analyses of a number of samples. Such reagent should be replenished manually by the operator. In order to replenish a reagent, a new reagent bottle is taken from a reagent storage place and a cap of the reagent bottle is opened so as to set the reagent bottle on the reagent disc. Alternatively, it is also possible to add a reagent into a reagent bottle set on the reagent disc from a bottle that contains a reagent for replenishment. During such replenishment of a reagent, it is also impossible to say conclusively that a reagent is never spilled by mistake.

In this embodiment, the printer 200 is disposed on the housing front wall 102. Thus, even when a sample or a reagent is spilled and accumulates on the housing upper face 100, there is no need to worry about sticking of the liquid accumulating on the housing upper face 100 to the printer 200 or a roll of paper ejected from the printer, which may otherwise contaminate the printed roll of paper. Nevertheless, when a certain amount of liquid is spilled on the housing upper face, there may be cases where the liquid drops to the housing side wall from the housing upper face or flows along the housing side wall, and thus contaminates the printing paper. However, even in such a case, it is possible to avoid contamination of the printing paper with the structure of this embodiment in which the printer 200 is disposed on the housing front wall 102 that is provided in a recessed manner from the front end 101 of the housing upper portion 100. That is, according to this embodiment, as the printer 200 is located on the inner side than the front end 101 of the housing upper portion and thus is protected by the eaves formed by the portions of the front end 101 of the housing upper portion 100, even if a sample or a reagent is spilled on the housing upper portion 100 and flows down from the front end 101 of the housing upper portion, there is no possibility that the sample or the reagent may stick to and contaminate the printer or the printed roll of paper ejected from the printer.

Next, a method of using the printer in this embodiment will be described. Typical examples of a method of using a printer attached to an automated analyzer includes a method of printing the analysis results of a sample. Examples of a method of printing the analysis results of a sample include a method of collectively printing analysis data for one day or one lot and a method of printing analysis results on a per-patient-basis. Thus, how to print analysis results with a printer depends on how a user of the automated analyzer uses the analysis results. When analysis data for one day or one lot is collectively printed, the analysis data is consecutively printed on a continuous roll of paper. If such a continuous roll of paper is kept hanging down from the printer, the roll of paper may eventually be scattered in folds on the floor and thus may become contaminated or disturb the operator who is operating the analyzer in front of the analyzer. Thus, in such a case, an end of the paper ejected from the printer 200 is guided to the entrance of the paper receptacle 210 with fingers or the like so that the printed paper is passed into the paper receptacle 210. Consequently, the printed paper is stored in the paper receptacle 210 in a clean state as indicated by the solid line 202 without hanging out of the analyzer, and thus without disturbing the operator. Meanwhile, if analysis results are to be printed on a per-patient-basis by performing an interrupt analysis, for example, printed paper can be guided to the outside of the paper receptacle 210 as indicated by the dashed line 203, and a desired printed portion can be cut out of the ejected paper with the cutter 204. The thus cut-out paper piece can be used by, for example, being stuck to a patient's medical record.

Further, as another method of using the printer, there is known a method of, when the remaining amount of a reagent loaded on the reagent disc has decreased, printing the name of the reagent, the reagent ID, and the like. As the size of the reagent bottle 121 is determined in advance, the control unit of the automated analyzer manages the remaining amounts of the respective reagent bottles by integrating the amounts of reagent suctioned from the individual reagent bottles by the reagent dispensing mechanism 150. Then, when the remaining amount of a reagent in a given reagent bottle has decreased, the control unit displays information to that effect on the display unit 160 to prompt the operator to prepare the reagent. Then, at timing necessary for replenishing the reagent, the control unit announces information on the display unit 160, for example, and stops the drive of the automated analyzer, and then outputs the name of the reagent to be replenished, the reagent ID, and the like to the printer to print such information. Then, the operator cuts a printed portion about the reagent out of the recording paper with the cutter 204, and takes the paper piece to a reagent storage place to precisely select a desired reagent from among a plurality of types of reagents and come back to the analyzer, and then replenishes the reagent bottle at a predetermined position on the reagent disc with the new reagent. Alternatively, the operator replenishes the reagent by replacing the reagent bottle with a decreased residual amount with a new reagent bottle brought with him/her. If the operator who has replenished the reagent leaves a paper piece with reagent information printed thereon in the reagent storage place, such information can be utilized for performing inventory control of reagents, an operation of placing an order for reagents, and the like.

Figure 6:
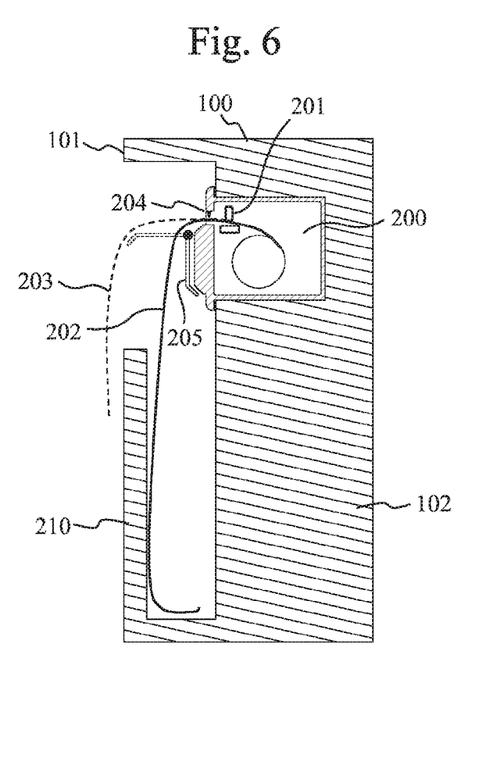
FIG. 6 is a schematic cross-sectional view of an example of a housing front wall, which includes a printer and a paper receptacle, and a housing upper portion connected thereto.

FIG. 6 is a schematic cross-sectional view of another example of the housing front wall, which includes the printer and the paper receptacle, and the housing upper portion connected thereto. The embodiment in FIG. 6 differs from the embodiment shown in FIG. 5 only in that the printer 200 has provided on the paper output unit thereof a flapper 205 as a means for switching the direction in which paper is ejected. The flapper 205 can be manually switched between a downward position indicated by the solid line and the horizontal position indicated by the dashed line. When a printed roll of paper is to be stored in the paper receptacle 210 as indicated by the solid line 202, the flapper 205 is placed in the downward position. Meanwhile, when a printed roll of paper is to be extracted to the outside of the paper receptacle 210 as indicated by the dashed line 203, the flapper 205 is placed in the horizontal position. When the flapper 205 is placed in the horizontal position, it becomes possible to extract printed paper without storing it in the paper receptacle 210 and without putting fingers or the like on the paper.

Figure 7:
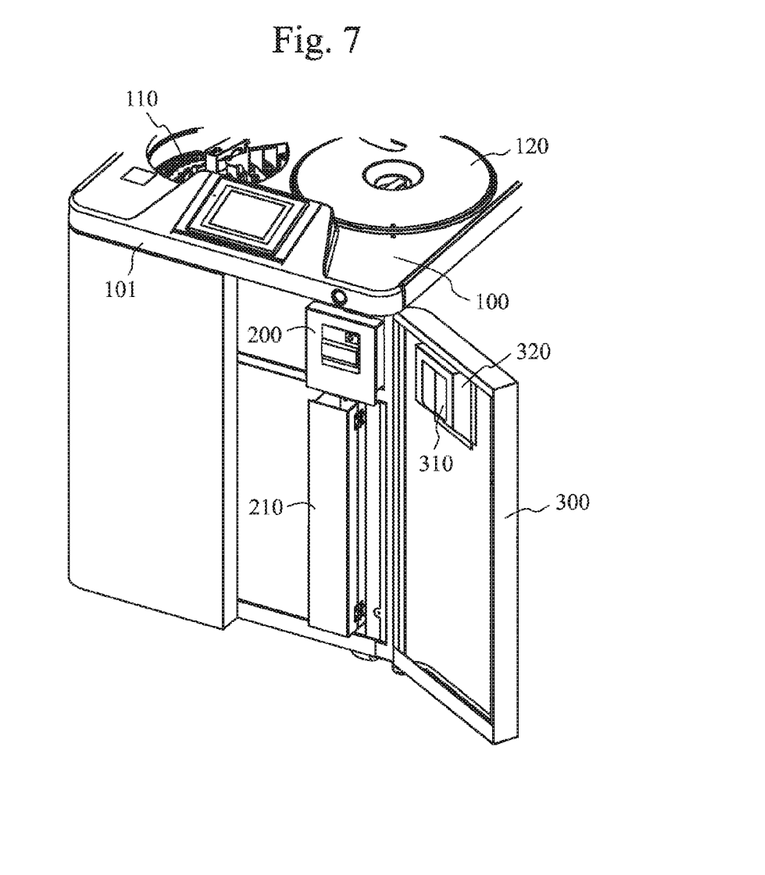
FIG. 7 is a schematic view of an embodiment of an automated analyzer having a front door.

FIG. 7 is a schematic view of another embodiment of the automated analyzer in accordance with the present invention. The housing front wall 102 of the automated analyzer is provided such that it is recessed from the front end 101 of the housing upper portion 100, and the front end 101 of the housing upper portion 100 thus projects like eaves above the housing front wall 102 as in the embodiment shown in FIG. 4. The housing front wall 102 has the printer 200 disposed thereon, and also has the paper receptacle 210 disposed below the printer 200. The paper ejection unit of the printer 200 is located at a position that is closer to the housing side than is the front end 101 of the housing upper portion 100. The automated analyzer in this embodiment has a front door 300 capable of covering the housing front wall 102. The front door 300 is attached in an openable/closable manner to the housing with hinges. The front door 300 has an opening 310 that allows paper ejected from the printer 200 to pass therethrough in a state in which the front door 300 is closed.

Figure 8:
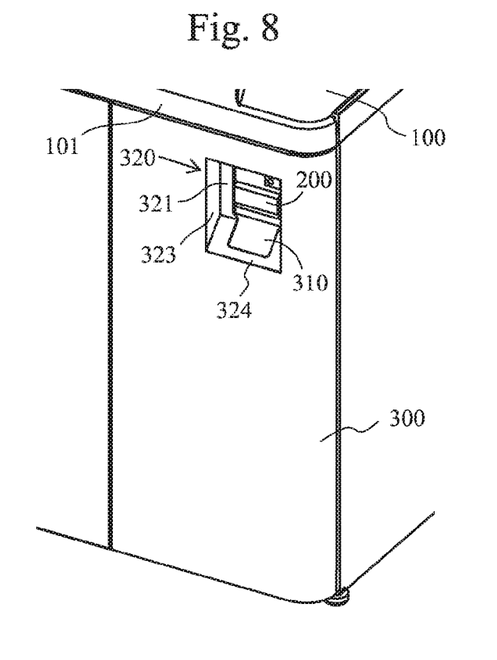
FIG. 8 is a schematic view illustrating a state in which the front door is closed.
Figure 9:
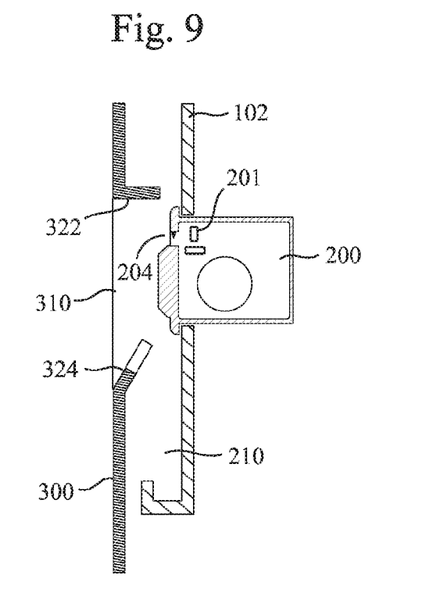
FIG. 9 is a schematic cross-sectional view illustrating a state in which the front door is closed.

FIG. 8 is a schematic view illustrating a state in which the front door is closed, and FIG. 9 is a schematic cross-sectional view illustrating a state in which the front door is closed. The front door 300 has a window 320, which is recessed from the door front face, at a portion corresponding to the printer 200 disposed on the housing front wall 102, and has an opening 310 formed in the window 320. The window 320 has a bottom face 321, which is positioned so as to be opposite the printer 200, an upper face 322, right and left side faces 323, and a lower face 324. The upper face 322, the right and left side faces 323, and the lower face 324 connect the surface of the front door 300 with the bottom face 321. The opening 310 is provided across the bottom face 321 and the lower face 324. Herein, the lower face 324 is formed such that it is tilted downward from the bottom face 321 toward the door front face, and has a frame shape in which the opening 310 is surrounded from the sides of the right and left side faces and the door front face, with one side of the frame open.

In the automated analyzer in this embodiment, when the front door 300 is open as illustrated in FIG. 7, the front end portion of the housing upper portion 100 that is located above the printer 200 serves as eaves for the printer 200 and the paper receptacle 210. Therefore, even when a liquid is spilled on the housing upper portion 100 and drops beyond the front end 101 of the housing upper portion 100, there is no possibility that the printer 200 or a printed roll of paper stored in the paper receptacle 210 may become wet. Meanwhile, when the front door 300 is closed as illustrated in FIG. 8, the upper face 322 of the window 320 provided in the front door 300 serves as eaves for the printer 200 and the paper receptacle 210 in a similar way. Thus, even when a liquid spilled on the housing upper portion 100 has flowed down along the surface of the front door 300, there is no possibility that that the printer 200, which is located at a position recessed from the door front face with the window 320 of the front door 300 interposed therebetween, or a printed roll of paper stored in the paper receptacle 210 may become contaminated.

The lower face 324 of the window 320 is formed such that it is tiled downward from the door back side toward the door front face, and the opening 310 is formed with margins left on the sides of the door front face and the right and left side faces. Therefore, when printed paper of the printer 200 is to be extracted through the front door 300, the margin portion on the door front face side of the lower face 324 of the window 320 serves as a guide. Thus, the printed paper can be smoothly extracted through the window 320. Meanwhile, when a printed roll of paper ejected from the printer 200 is to be stored in the paper receptacle 210 located on the back side of the closed front door 300, it is acceptable as long as an end of the roll of paper ejected from the printer 200 is guided into the opening 310 with fingers or the like.

Figure 10:
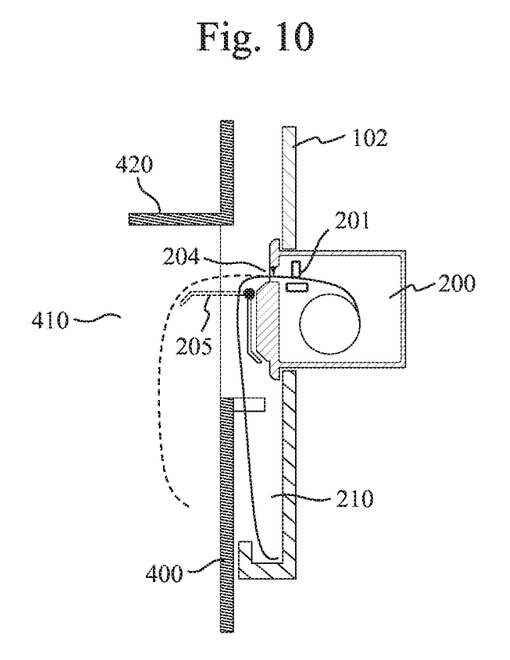
FIG. 10 is a schematic cross-sectional view of an embodiment of an automated analyzer having a front door.

FIG. 10 is a schematic cross-sectional view of an embodiment of an automated analyzer having a front door with a different shape. A front door 400 in this embodiment has an opening 410 at a position corresponding to the printer 200 disposed on the housing front wall 102. Eaves 420 are formed at an upper end of the opening 410 such that they project beyond the door front face.

In this embodiment also, when the front door 400 is open, the front end portion of the housing upper portion 100 located above the printer 200 serves as eaves for the printer 200 and the paper receptacle 210. Therefore, even when a liquid is spilled on the housing upper portion 100 and drops beyond the front end 101 of the housing upper portion 100, there is no possibility that the printer 200 or a printed roll of paper stored in the paper receptacle 210 may become wet. Meanwhile, when the front door 400 is closed, the eaves 420 formed on the front door 400 are present. Thus, even when a liquid spilled on the housing upper portion 100 has flowed down along the surface of the front door 400, such liquid is shielded by the eaves 420. Thus, there is no possibility that the printer 200 or printed paper stored in the paper receptacle 210 may become contaminated.

It is also possible to provide the paper output unit of the printer 200 with the flapper 205 as a means for switching the direction in which paper is ejected. When a printed roll of paper is to be stored in the paper receptacle 210 as indicated by the solid line, the flapper 205 is placed in the downward position. Meanwhile, when a printed roll of paper is to be extracted through the opening 410 of the front door 400 as indicated by the dashed line, the flapper 205 is placed in the horizontal position. When the flapper 205 is placed in the horizontal position, it becomes possible to extract a printed roll of paper through the opening 410 of the front door 400 without putting fingers or the like on the paper.

It should be noted that the present invention is not limited to the aforementioned embodiments, and includes a variety of variations. For example, although the aforementioned embodiments have been described in detail to clearly illustrate the present invention, the present invention need not include all of the configurations described in the embodiments. It is possible to replace a part of a configuration of an embodiment with a configuration of another embodiment. In addition, it is also possible to add, to a configuration of an embodiment, a configuration of another embodiment. Further, it is also possible to, for a part of a configuration of each embodiment, add, remove, or substitute a configuration of another embodiment.

REFERENCE SIGNS LIST

100 Housing upper potion
101 Front end of housing upper potion
102 Housing front wall
110 Sample disc
111 Sample cup
120 Reagent disc
121 Reagent bottle
130 Reaction disc
131 Reaction cell
140 Sample dispensing mechanism
150 Reagent dispensing mechanism
160 Display unit
170 Transmitted light beam measurement unit
200 Printer
205 Flapper
210 Paper receptacle
300 Front door
310 Opening
320 Window
400 Front door
410 Opening
420 Eaves

The invention claimed is:

1. An automated analyzer comprising:

a housing upper portion, the housing upper portion having disposed thereon a sample disc holding a plurality of samples, a reagent disc holding a plurality of types of reagents, a reaction disc holding a plurality of reaction cells, a sample dispensing mechanism for dispensing one of the samples into one of the reaction cells held on the reaction disc, and a reagent dispensing mechanism for dispensing one of the reagents into the reaction cell held on the reaction disc;

a housing front wall provided in a recessed manner from a front end of the housing upper portion; and a printer disposed on the housing front wall;

a paper receptacle disposed on the housing front wall below the printer to receive paper ejected from the printer;

a front door which is openable and closeable, the front door covering the housing front wall that has the printer and the paper receptacle disposed thereon, and the front door has a window formed in a recessed manner from a door front face of the front door at a position corresponding to the printer, wherein the window is defined by a bottom face, an upper face, right and left side faces, and a lower face, wherein the bottom face is disposed opposite the printer, and the upper face connects the door front face with the bottom face, wherein the bottom face and the lower face define an opening provided across the bottom face and the lower face, and the opening allows the paper ejected from the printer to pass therethrough in a state in which the front door is closed, and wherein the printer includes a flapper that moves to switch an ejection direction in which the paper is ejected from the printer.

2. The automated analyzer according to claim 1, wherein the lower face is tilted downward from the bottom face toward the door front face, and has a frame shape in which the opening is surrounded from sides of the right and left side faces and the door front face.

* * * * *